United States Patent [19]
Mendes et al.

[11] Patent Number: 5,500,009
[45] Date of Patent: *Mar. 19, 1996

[54] METHOD OF TREATING HERPES

[75] Inventors: Emanuel Mendes, Petach Tikva; Avikam Harel, Tel Aviv, both of Israel

[73] Assignee: Amron, Ltd., Tel Aviv, Israel

[ * ] Notice: The term of this patent shall not extend beyond the expiration date of Pat. No. 5,259,380.

[21] Appl. No.: 126,583

[22] Filed: Sep. 27, 1993

Related U.S. Application Data

[63] Continuation-in-part of Ser. No. 615,050, Nov. 15, 1990, Pat. No. 5,259,380.

[51] Int. Cl.$^6$ .................................................. A61N 5/06
[52] U.S. Cl. ........................ 607/88; 606/9; 606/3
[58] Field of Search .................... 607/88–90; 606/1–3, 606/13, 9

[56] References Cited

U.S. PATENT DOCUMENTS

| | | |
|---|---|---|
| 4,535,784 | 8/1985 | Rohlicek et al. . |
| 4,646,743 | 3/1987 | Parris . |
| 4,930,504 | 6/1990 | Diamantopoulos et al. ........... 606/3 X |

FOREIGN PATENT DOCUMENTS

| | | |
|---|---|---|
| 2212010 | 7/1989 | United Kingdom . |

OTHER PUBLICATIONS

Mester et al, "The Biomedical Effects of Laser Application", Lasers in Surgery and Medicine 5, 31–39, 1985.
Notkins A. L. et al, "Workshop on the Treatment and Prevention of Herpes Simplex Virus Infections". J. Infect. Dis. 127: 117–119, 1973.
Embil J. A. et al, "Prevalence of Recurrent Herpes Labialis and Apthous Ulcers Among Young Adults on Six Continents". Can. Med. Assoc. J. 113: 627–630, 1975.
Young S. K. et al, "A Clinical Study for the Control of Facial and Mucocutaneous Herpes Virus Infections; Characterization of Natural . . . ". Oral Surg. 41: 496–507, 1976.
Spotswood L. et al, "The Natural History of Recurrent Herpes Simplex Labialis". N. Eng. J. of Med. 297 (2) 69–75, 1977.
Young S. et al, "Macrophage Responsiveness to Light Therapy", Lasers in Surg. and Med. Supplement 1991 by John Wiley & Sons, Ltd.
Calderhead G. R., Review of the Biostimulation Session of the 11th Meeting of the American Society for Laser Medication and Surgery (ASLMS). Lasers in Surgery and Medicine, Suppl. 3, 1991, pp. 10–12.
Mester, A. F. and Mester A. R., "Scientific Background of Laser Biostimulation", Laser1(1) 23, 1988.
Karu, T. I., "Molecular Mechanisms of the Therapeutic Effect of Low–Intensity Laser Irradiation". Lasers in Life Sciences, 2(1) 5374, 1988.
Abergal, R. P., "Biostimulation of Wound Healing by Lasers: Experimental Approaches in Animal Models and Fibroblast Cultures". J. of Dermatology and Surgical Oncology, 13,127,1987.

*Primary Examiner*—Angela D. Sykes
*Attorney, Agent, or Firm*—Natter & Natter

[57] ABSTRACT

A method of treating herpes by illuminating a herpes affected dermal zone with continuous wave (CW) non-coherent radiation emitted by at least one light emitting diode (LED), the radiation having a narrow bandwidth centered at a wavelength suitable for herpes treatment, and maintaining the light radiation for a prescribed treatment duration.

15 Claims, 2 Drawing Sheets

METHOD OF TREATING HERPES

RELATED APPLICATIONS

This application is a continuation-in-part of application Ser. No. 615,050, filed Nov. 15, 1990, now U.S. Pat. No. 5,259,380.

FIELD OF THE INVENTION

The present invention relates to apparatus and a method for treatment of herpes.

BACKGROUND OF THE INVENTION

Herpes infections, primarily occurring on the lips or genital areas, are among the most common viral infections in humans, affecting all races and both sexes. Herpes infections are annoying, disfiguring and sexually inhibiting. Recurrence of the disease is estimated to occur in 20 to 40 percent of the population.

Many forms of topical treatment have been tried in the past although none have been shown to be consistently effective as described in the following reference, the disclosure of which is hereby incorporated by reference herein:

Spotswood L., Spruance M. D. et. al., The Natural History of Recurrent Herpes Simplex Labialis, *New England Journal of Medicine* 297 [2] 69–75, 1977.

Laser therapy is known for treating a variety of patient complaints and ailments. In particular, the therapeutic effects of laser light therapy on wound healing are well known as described in the following references, the disclosures of which are hereby incorporated by reference herein:

Calderhead, Glen R., Review of the Biostimulation session of the 11th Meeting of the American Society for Laser Medication and Surgery (ASLMS), *Lasers in Surgery and Medicine*, Suppl. 3, 1991; and Master et. al., The Biomedical Effects of Laser Application, *Lasers in Surgery and Medicine* 5, 31–39, 1985.

Typically, low power helium neon lasers and minimum powered infrared lasers have been used to treat the surface of the body.

Use of light emitting diodes (LEDs) in administering light therapy is also known. A device suitable for administering light therapy is disclosed in U.S. Pat. No. 4,930,504 to Diamantopoulos et al. Diamantopoulos et al hypothesize that the disclosed device may be used, "for example, to treat inflammations, wounds, burns, chronic ulcerations including diabetic ulcers, deficient circulation, pain, nerve degeneration, eczema, shingles, infection, scars, acne, bone fractures, muscle and ligament injuries, arthritis, osteo-arthritis, rheumetiodal arthritis, skin grafts, gingival irritation, oral ulcers, dental pain and swelling, cellulitis, stretch marks, skin tone, alopecia areata, trigeminal neuralgia, herpes, zosten, sciatice, oervioal erosions and other conditions."

Diamantopoulos et al teach the use of an array of substantially monochromatic radiation sources of a plurality of wavelengths, preferably of at least three different wavelengths. The sources radiate in accordance with a high duty-cycle pulsed rate, and are arranged within the array such that radiation of at least two different wavelengths passes directly or indirectly through a single point located within the treated tissue.

Use of LEDs in administering light therapy for the treatment of certain ailments and complaints is disclosed in published UK Application GB 2212010A.

Related apparatus in the art include U.S. Pat. No. 4,535,784 which shows use of a single LED for stimulating acupuncture points. Furthermore, U.S. Pat. No. 4,646,743 shows the use of a plurality of LEDs for irradiating a larger area than a single diode can effectively irradiate.

SUMMARY OF THE INVENTION

The present invention seeks to provide a method for therapeutic illumination which are particularly suited for the treatment of herpes.

There is thus provided in accordance with a preferred embodiment of the present invention a method of relieving herpes by illumination including the steps of utilizing at least one light emitting diode (LED) by driving each of the at least one LED in a substantially continuous wave (CW) mode to generate light radiation in a narrow bandwidth centered at a wavelength suitable for herpes relief, and projecting the light to a herpes-affected dermal zone for biostimulative treatment thereof and maintaining the light radiation for a prescribed treatment duration.

In accordance with a preferred embodiment of the present invention there is also provided a method of relieving herpes by illumination including the steps of utilizing at least one light emitting diode (LED) emitting non-coherent light in a narrow bandwidth centered at a wavelength suitable for herpes relief, projecting the light to a herpes-affected zone for biostimulative treatment thereof and maintaining the light radiation for a prescribed treatment duration, wherein the light emitted by each of the plurality of diodes has substantially the same wavelength and wherein the herpes affected dermal zone is not simultaneously illuminated by biostimulating radiation of another wavelength.

Further in accordance with a preferred embodiment of the present invention, the plurality of LEDs is arranged along a plane and preferably includes one or more circular or linear arrays of LEDs.

Still further in accordance with a preferred embodiment of the present invention, the narrow bandwidth comprises a red light bandwidth having a wavelength of approximately 660 nm.

Still further in accordance with a preferred embodiment of the present invention, each of the LEDs emits a cone of light, and the LEDs are configured and arranged such that the plurality of cones of light emitted by the LEDs illuminates a common dermal area.

BRIEF DESCRIPTION OF THE DRAWINGS

The present invention will be understood and appreciated from the following detailed description, taken in conjunction with the drawings in which.

DETAILED DESCRIPTION OF PREFERRED EMBODIMENTS

Figure 1:
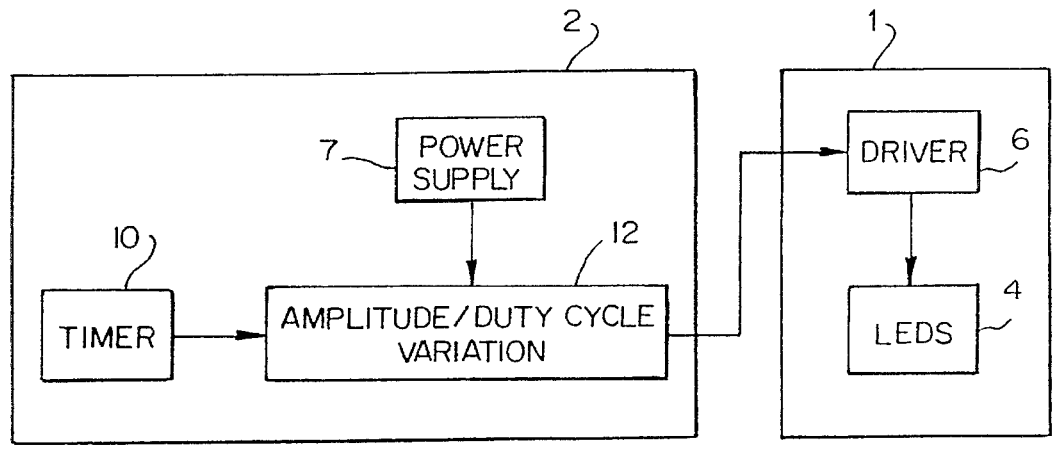
FIG. 1 is a simplified block diagram functionally showing apparatus constructed and operative in accordance with a preferred embodiment of the present invention.

Referring to FIG. 1 which is a block diagram of a device for performing the therapeutic method of the invention, there is shown a compact light source 1 and an associated control unit 2 which preferably has a CW (continuous wave)

mode of operation. Light source 1 comprises a plurality of LEDs 4 which receive power via a driver circuit 6. Preferably, each of LEDs 4 emits light of substantially the same frequency. Control unit 2 contains a power supply 7 and a timer 10 which can be constituted by a standard clock circuit provided with "set time" switches, and whose function is to disable the control circuit 2 after a preset time has elapsed.

Optionally, an amplitude and/or duty cycle variation circuit 12 provides a voltage with a variable amplitude and/or duty cycle which is fed to the driver 6 of the light source 1. Thus, the light source 1 emits light with a magnitude and/or duty cycle determined by amplitude/duty cycle variation circuit 12.

Figure 2:
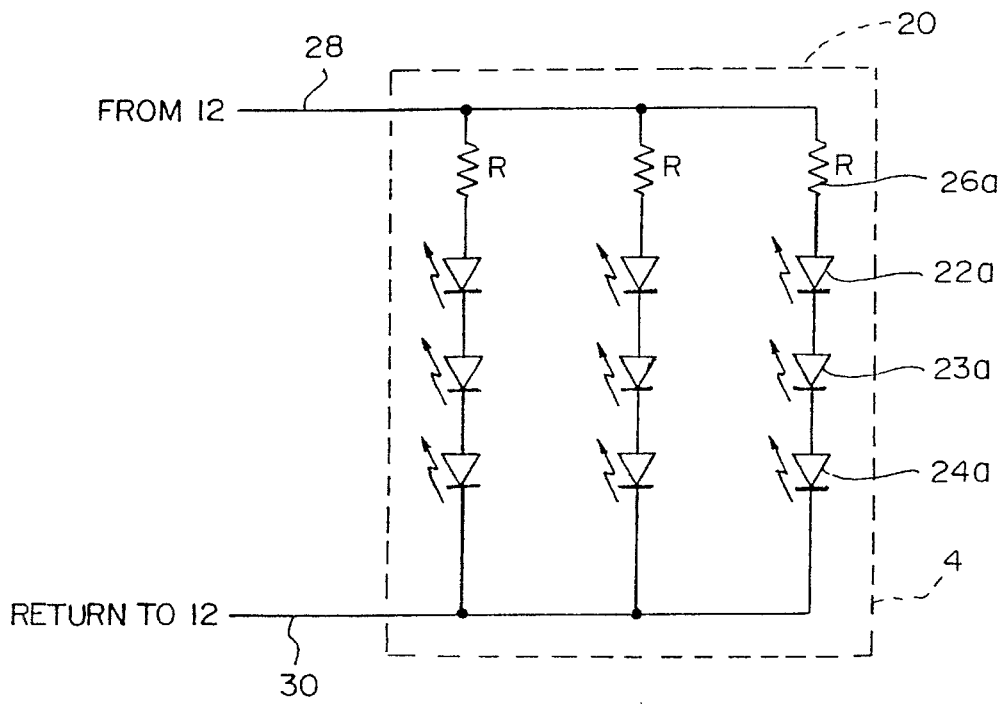
FIG. 2 shows the LEDs of FIG. 1 in greater detail.

FIG. 2 shows a preferred arrangement of LEDs 4 (of FIG. 1). LEDs 4 are arranged in the form of an LED matrix 20 comprising a plurality of parallel branches each of which contains a predetermined number of LEDs connected in series. Thus, in FIG. 2, three LEDs 22a, 23a and 24a are connected in series and constitute one parallel branch of the diode matrix 20. The current flowing through this branch is limited by means of a series resistor 26a, and the resulting branch is connected between a high voltage d.c. rail 28 and a low voltage d.c. rail 30. Thus, one terminal of the series connected current-limiting resistor is connected to the high voltage rail whilst the cathode of LED 24a is connected to the low voltage rail 30. The connection of all other branches of the LED matrix 20 is identical.

According to an alternative embodiment, series resistor 26a may be omitted and the LEDs driven by a current source.

Figure 3:
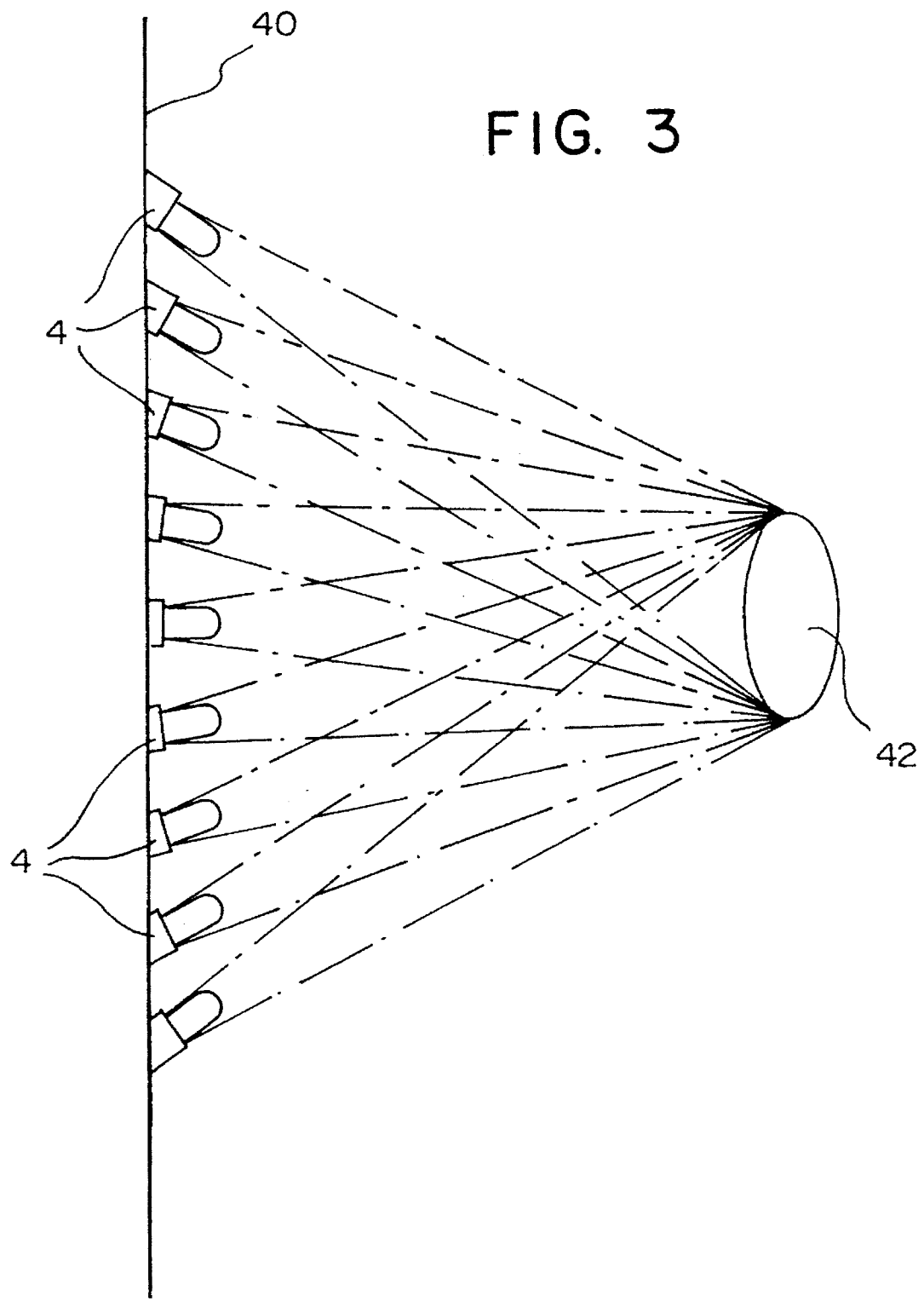
FIG. 3 shows a preferred arrangement for the physical connections of the LEDs shown schematically in FIG. 2.

FIG. 3 shows a preferred arrangement for the physical connections of the LEDs shown schematically in FIG. 2. The LEDs 4 are preferably disposed on a planar surface 40, and are arranged along and angled with respect to the planar surface, such that their light outputs illuminate a defined area 42 such as a herpes-afflicted portion of skin. In a preferred embodiment, the area 42 which the LEDs illuminate is substantially circular with a diameter of approximately 1.2 cm. The LEDs may be arranged in any suitable manner on planar surface 40, such as in one, two or more concentric circles, or in one or more linear arrays. The greater the number of LEDs connected within the LED matrix 20 of FIG. 2, the greater will be the intensity of the light output by the light source 1 (FIG. 1).

Each of the LEDs emits a come of light, and the LEDs are configured and arranged such that the plurality of cones of light emitted by the plurality of LEDs intersects over the area 42, thereby concentrating their illumination on area 42.

The operation of the system is as follows. The amplitude and/or duty cycle variation circuit 13 operates so as to provide d.c. voltage with variable amplitude and/or duty cycle between the high voltage supply rail 28 and the ground terminal 30. Thus, by varying the setting of the amplitude/duty cycle variation circuit 12, the overall current flowing through the LED matrix 20 may be varied, and, therefore, the light intensity of the light source 1 may be varied. As mentioned above, it is preferred that variation circuit 12 is set to a substantially continuous-wave mode of operation.

A preferred power level is approximately 10–30 mW/cm$^2$, such as 20 mW/cm$^2$ projected onto the area of treatment.

The invention affords low cost apparatus for treating herpes by producing a non-coherent source of illumination, preferably in CW mode, which is focussed over a small area. The exact wave-length of the illumination is confined within a relatively narrow bandwidth (–/+25 nm) and its central value may be predetermined by suitable selection of the LEDs in the LED matrix 20. Experimental evidence indicates that red light, such as 660 nm light, is particularly suitable for the treatment of herpes. The average intensity of the emitted illumination may easily be varied by the operator, and the therapy time may be preset by means of the integral timer circuit which is preferably provided.

It will be appreciated that the particular features of the methods and apparatus shown and described herein may be employed separately or in combination in any suitable manner so as to enhance efficacy of treatment.

Variations on the apparatus shown and described herein are disclosed in Published UK application GB 2212010A. However, it is believed that the embodiment described hereinabove with reference to FIGS. 1–3 is a preferred embodiment for treatment of herpes. Supporting experimental results are now described:

An experimental study was carried out to evaluate the therapeutic effect of non-coherent, low level, narrow band LED Light Therapy (hereinafter LLT) at a wavelength of approximately 660 nm on the course of herpetic skin disease. The LLT treatment was compared to other topical and/or systemic treatments used on previous herpetic attacks in the same patient.

Eighteen patients suffering from recurrent herpetic infections, either labial or progenitalia, for at least one year, were selected for the study. The age of the patients ranged from 8 to 60 (mean age 29.1) and frequency of reoccurrance ranged from twice a year to 12 times a year (mean 5.1). The patients were in good physical condition and no medication other than birth control pills was allowed to be taken during the study. Patients were asked to appear for entry in the study as soon as possible after the onset of the herpetic skin lesion or even in the prelesion stage, when only the sensation of itching was present in the area.

A hand held emitter of LLT 660 nm radiation was provided to patients for home use, 3 times daily for ten minutes each time. Time to loss of crust and patients' judgement of healing were criteria used to evaluate efficacy as compared with topical and/or systemic treatments used in previous attacks.

The average duration of a single attack using the LLT treatment was 3.13 days (SD=1.29) as compared with 10.68 days (SD=3.47) as reported by patients when topical treatment was used in previous attacks. This difference was examined by 1-way repeated measures (ANOVA) and proved to be statistically significant.

Patients who began the treatment in the prelesions stage (4 patients) reported a significant alteration of the course of the disease. A blister never developed. Burning, itching and pain in the area was limited to the first 24 hours, if at all. The remaining 14 patients who began treatment in the vesicle stage reported significantly less pain and no secretion or ulceration as they had experienced in previous attacks.

When asked their subjective impression, 64.3% defined LLT treatment as excellent; 14.3% defined it as very good; and 21.4% defined it as good. None of the patients defined the LLT treatment as worse or fair. No side effects were reported.

Thus, LED 660 nm light therapy treatment has been proven to alter the course of herpetic skin lesion, to be more effective than conventional topical antiviral treatments, and to be more acceptable as an antiviral treatment by the patient.

It will be appreciated by persons skilled in the art that the present invention is not limited to what has been particularly shown and described hereinabove. Rather, the scope of the present invention is defined only by the claims that follow.

We claim:

1. A method of treating herpes with red light radiation, the method comprising the steps of:
   (a) providing a plurality of light emitting diodes which generate non-coherent radiation in a narrow bandwidth centered at a wavelength of approximately 660 nm,
   (b) driving the diodes to generate the non-coherent radiation in a continuous wave mode,
   (c) concentrating and projecting the non-coherent radiation on a dermal area afflicted with herpes without simultaneously illuminating the area with non-coherent light emitting diode radiation centered about a different wavelength and
   (d) maintaining the concentrating and projecting step (c) for a prescribed treatment duration.

2. A method of treating herpes with red light radiation in accordance with claim 1 wherein the radiation is concentrated and projected on the area afflicted with an illumination power in the range of between 10 and 30 mw/cm$^2$.

3. A method of treating herpes with red light radiation in accordance with claim 2 wherein the substantially circular pattern has a diameter in the order of 1 cm.

4. A method of treating herpes with red light radiation in accordance with claim 3 wherein the diameter is in the order of 1.2 cm.

5. A method of treating herpes with red light radiation in accordance with claim 1 wherein the radiation is concentrated and projected in a substantially circular pattern.

6. A method of treating herpes with red light radiation in accordance with claim 1 wherein the treatment duration is in the order of 8 to 12 minutes.

7. A method of treating herpes with red light radiation in accordance with claim 6 wherein step (b), step (c) and step (d) are repeated at least once per day for a cumulative daily treatment duration in the order of 16 to 48 minutes per day.

8. A method of treating herpes with red light radiation in accordance with claim 7 wherein the cumulative daily treatment duration is in the order of 30 minutes per day.

9. A method of treating herpes with red light radiation in accordance with claim 1 wherein the step of driving the diodes to generate non-coherent radiation in a continuous wave mode includes the step of controlling the intensity of the non-coherent radiation by controlling the amplitude and duty cycle at which the light emitting diodes are being driven.

10. A method of treating herpes with red light radiation in accordance with claim 1 wherein the step of concentrating and projecting the non-coherent radiation includes the step of mounting the plurality of diodes in a planar array.

11. A method of treating herpes with red light radiation in accordance with claim 10 wherein the step of mounting includes mounting the plurality of diodes in at least one circular array.

12. A method of treating herpes with red light radiation in accordance with claim 10 wherein the step of mounting includes mounting the plurality of diodes in at least one linear array.

13. A method of treating herpes with red light radiation in accordance with claim 1 wherein the steps of driving the diodes to generate the non-coherent radiation, concentrating and projecting the non-coherent radiation and maintaining the concentrating and projecting steps for a prescribed treatment duration are repeated daily for the duration of a herpetic lesion.

14. A method of treating herpes with red light radiation in accordance with claim 1 wherein the steps of driving the diodes to generate the non-coherent radiation, concentrating and projecting the non-coherent radiation and maintaining the concentrating and projecting steps for a prescribed treatment duration are commenced prior to the onset of a visible herpetic lesion.

15. A method of treating herpes with light radiation, the method comprising the steps of:
   (a) providing a plurality of light emitting diodes which generate non-coherent radiation in a narrow bandwidth centered at a wavelength suitable for herpes treatment,
   (b) driving the diodes to generate the non-coherent radiation in a continuous wave mode,
   (c) concentrating and projecting the non-coherent radiation on a dermal area afflicted with herpes without simultaneously illuminating the area with non-coherent light emitting diode radiation centered about a different wavelength, and
   (d) maintaining the concentrating and projecting step (c) for a prescribed treatment duration.

* * * * *